(12) United States Patent
Gulian et al.

(10) Patent No.: US 8,631,533 B1
(45) Date of Patent: Jan. 21, 2014

(54) FOOTWEAR CLEANER AND DISINFECTANT

(75) Inventors: Ana M. Gulian, Chadds Ford, PA (US); Paul M. Gulian, Chadds Ford, PA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 400 days.

(21) Appl. No.: 13/161,536

(22) Filed: Jun. 16, 2011

(51) Int. Cl.
*A47L 23/02* (2006.01)

(52) U.S. Cl.
USPC .................................. 15/36; 15/97.2

(58) Field of Classification Search
USPC .............................. 15/36–37, 97.2
See application file for complete search history.

(56) References Cited

U.S. PATENT DOCUMENTS

| | | | | |
|---|---|---|---|---|
| 2,726,414 A | * | 12/1955 | Lindquist | 15/4 |
| 4,014,060 A | * | 3/1977 | Taylor | 15/36 |
| 4,432,112 A | * | 2/1984 | Muller et al. | 15/36 |
| 5,545,257 A | | 8/1996 | Vella | |
| 5,964,959 A | * | 10/1999 | Bleth | 134/32 |
| 6,813,810 B2 | * | 11/2004 | Beynon | 15/406 |
| 8,512,631 B2 | * | 8/2013 | Kerr | 422/24 |
| 2009/0038096 A1 | | 2/2009 | Hollander | |
| 2010/0193709 A1 | | 8/2010 | Dalton | |

FOREIGN PATENT DOCUMENTS

JP       2010-82085 A   *   4/2010   ............. A47L 23/02

* cited by examiner

*Primary Examiner* — Laura C Guidotti
(74) *Attorney, Agent, or Firm* — Dave A. Ghatt

(57) ABSTRACT

An apparatus for cleaning and disinfecting footwear or the foot of a user. More particularly, a user controlled multi-functioning device that performs both cleaning and disinfecting of footwear upon contact. The cleaning and disinfecting apparatus includes one or more cleaning rollers physically contacting the footwear or foot and one or more disinfectant sources, which may be radiation sources that emits UV rays e.g., or charge particle source that emits a cold plasma blast.

5 Claims, 3 Drawing Sheets

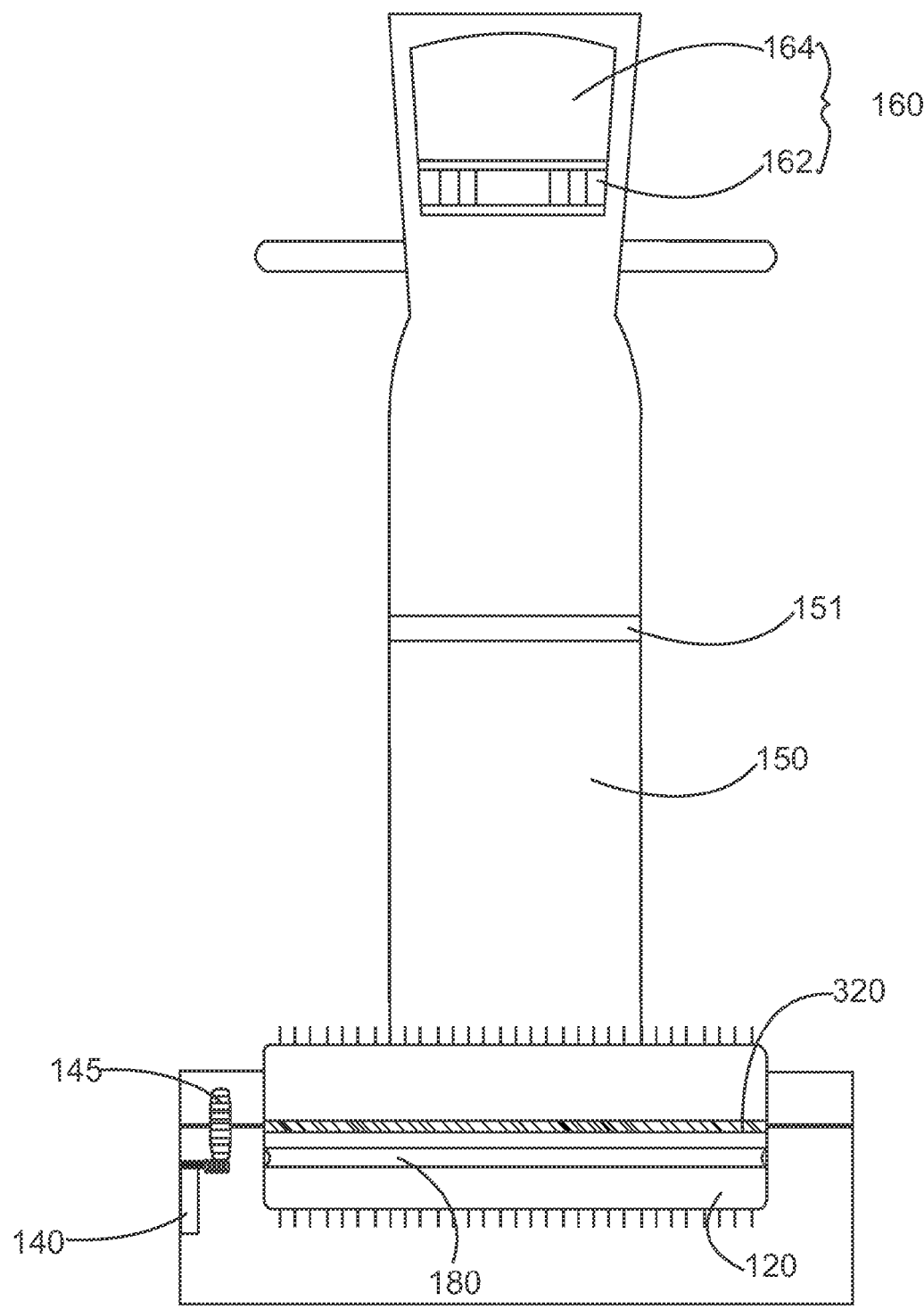

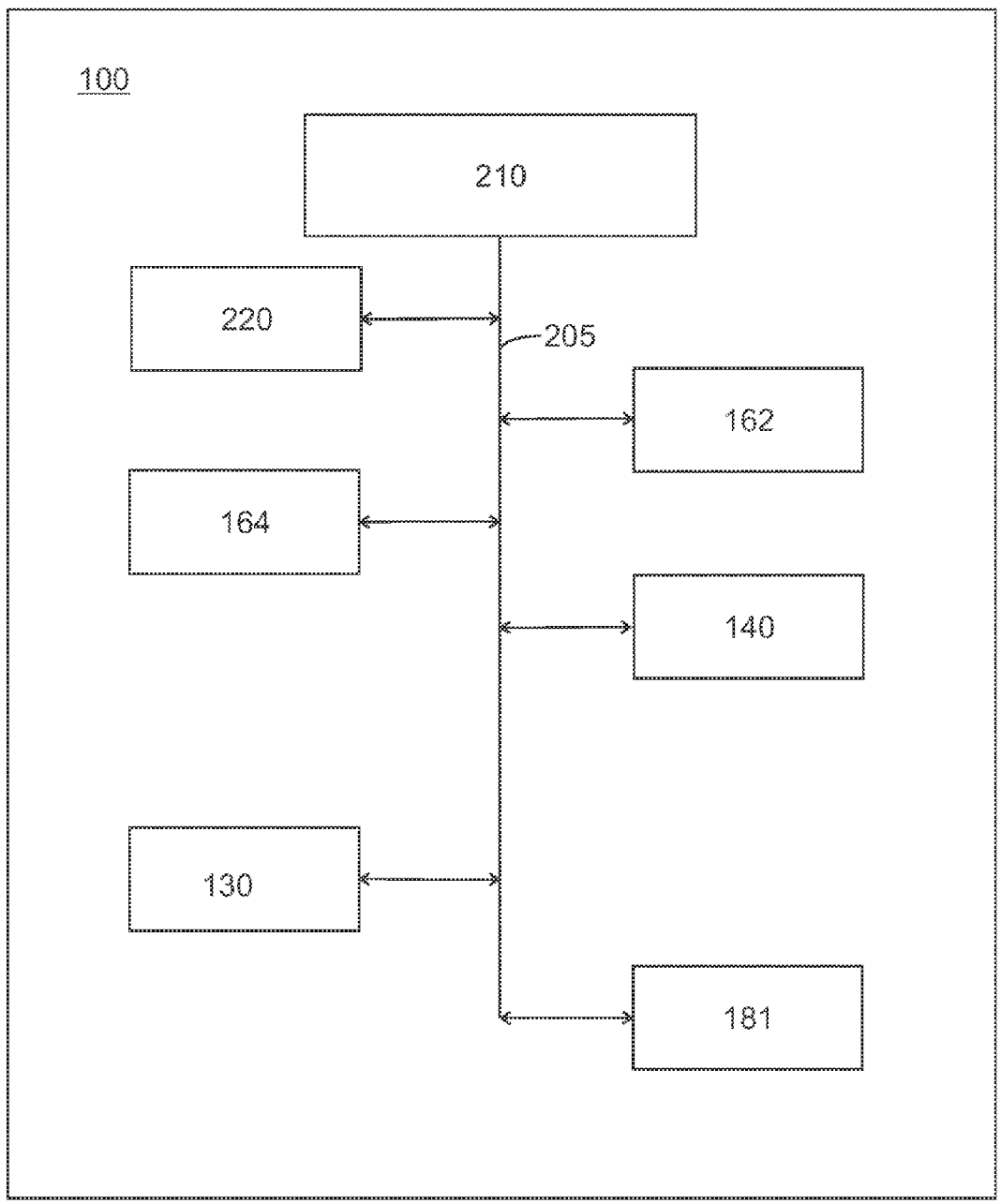

FOOTWEAR CLEANER AND DISINFECTANT

STATEMENT OF GOVERNMENT INTEREST

The following description was made in the performance of official duties by employees of the Department of the Navy, and, thus the claimed invention may be manufactured, used, licensed by or for the United States Government for governmental purposes without the payment of any royalties thereon.

TECHNICAL FIELD

The following description relates generally to an apparatus for cleaning and disinfecting footwear. More particularly, a user controlled multi-functioning device that performs both cleaning and disinfecting of footwear upon contact.

BACKGROUND

Infectious diseases can be spread by shoe traffic and the handling of footwear. One study found that up to about 421,000 units of bacteria may reside on the outside of a shoe. Some of the bacteria found are known for causing intestinal and bloodstream infections, bacterial meningitis and pneumonia. The spread of infectious diseases is highlighted in situations where one moves from one location that houses these bacteria, to another location with organisms that are susceptible to these bacteria. For example, visitors to livestock and agricultural facilities can transmit diseases to the vulnerable livestock and agriculture. Similar risks exist because of shoe traffic to and from medical facilities, residential homes, day cares, schools, and vehicles, particularly vehicles that travel internationally, such as airplanes and cruise and cargo ships.

As a solution to this problem, the prior art teaches the use of mats, liquid cleaners and disinfectants, spray-on disinfectants, and the use of pressurized water. These devices all teach cleaning and/or disinfecting of footwear by a single cleaning or disinfecting means. The prior art does not teach a multi-functioning device capable of thoroughly cleaning the footwear by using a combination of cleaning techniques.

SUMMARY

In one aspect, the invention is a cleaner and disinfectant apparatus for footwear. In this aspect, the cleaner and disinfectant includes a support base having an upper surface having an upper surface window, a lower surface, one or more side surfaces, and a hollow interior within the upper surface, the lower surface, and the one or more side surfaces. The cleaner and disinfectant also includes a plurality of spaced-apart rotatable elongated brushes positioned within the hollow interior of the support base. According to the invention, at least a portion of the each of the plurality of the spaced-apart rotatable elongated brushes extends through the upper surface. The cleaner and disinfectant apparatus also includes a plurality of spaced-apart disinfectant sources projecting one of UV radiation, nano UV radiation, cold plasma, or non-thermal plasma through the upper surface window of the support base.

BRIEF DESCRIPTION OF THE DRAWINGS

Other features will be apparent from the description, the drawings, and the claims.

FIG. 3 is an exemplary sectional front view of a cleaning and disinfecting apparatus through line 3-3 of FIG. 2; and FIG. 4 is an exemplary block diagram of a cleaning and disinfecting apparatus, according to an embodiment of the invention.

DETAILED DESCRIPTION

Figure 1:
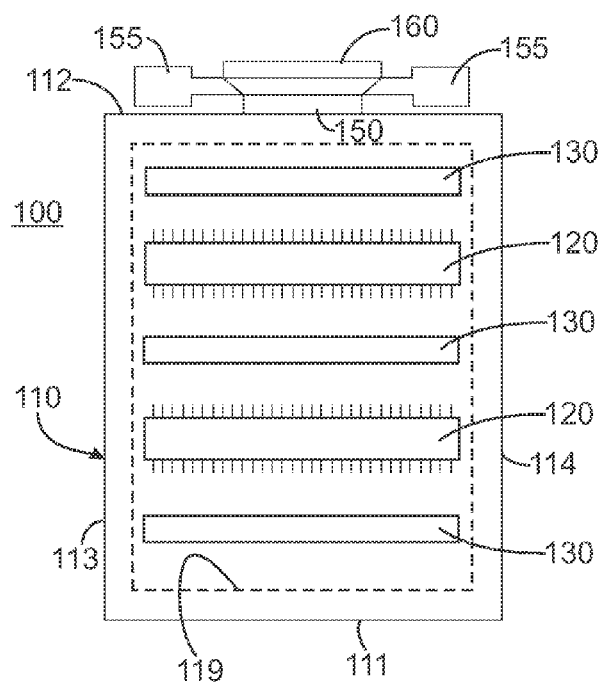
FIG. 1 is an exemplary perspective top view of a cleaning and disinfecting apparatus, according to an embodiment of the invention.

FIG. 1 is an exemplary perspective top view of a cleaning and disinfecting apparatus 100, according to an embodiment of the invention. As outlined below, the cleaning and disinfecting apparatus 100 is provided for cleaning and/or sanitizing footwear. The apparatus 100 may be removably positioned or fixed at any desired location to provide the cleaning and/or disinfecting service. For example, the cleaning and disinfecting apparatus 100 may be positioned at the entrance or within a permanent or temporary medical facility, an agricultural facility, a government building, a daycare building, a residential building, an aircraft, a cruise or cargo ship, or a train.

As shown, the cleaning and disinfecting apparatus 100 includes a support base 110 having a front side 111, a back side 112, and lateral sides 113 and 114. As shown in FIG. 1, the apparatus also includes a plurality of spaced-apart cleaning rollers 120, which as outlined below, are rotatably mounted within the support base 110. Each roller 120 may include brushes or bristles, thereby forming an elongated brush, to enhance cleaning. FIG. 1 also includes a plurality of spaced-apart disinfectant sources 130, which may be a radiation source or a charged particle source. A radiation source may be a UV tube providing UV rays or nano UV rays for killing bacteria and other germs. A charged particle source may be a cold plasma gun or a non-thermal plasma gun which emit an ionized gas that kills harmful bacteria and germs. Whatever the type, the source 130 is preferably positioned to release the disinfectant medium so that it strikes the footwear at about 90 degrees in order to optimize the disinfecting process.

As shown in FIG. 1, the cleaning rollers 120 and the disinfectant sources are arranged in an alternating array. This alternating arrangement optimizes cleaning and disinfecting by allowing the charged particle disinfectant or the radiation disinfectant access to bacteria and other germs, as dirt, dust, bacteria, and other micro particles are being physically removed by the rotation of the cleaning rollers 120. FIG. 1 shows an alternating arrangement having two spaced-apart cleaning rollers 120 and three spaced-apart disinfectant sources 130. It should be noted that depending on the requirements, other alternating arrangements may be utilized. For example, the cleaning and disinfecting apparatus 100 may be an arrangement having only one cleaning roller 120 flanked by two disinfectant sources 130, or for example, the apparatus 100 may have three cleaning rollers 120 in an alternating arrangement with four disinfectant sources 130.

It should be noted that the disinfectant source 130 may be selected based on the application. Thus, in situations where cold plasma particles are most effective, a cold plasma source would be selected, as opposed to a UV source. Alternatively, there may be situations where it is desired to have different types of disinfectant used simultaneously. Thus for example, in such a situation, the illustration of FIG. 1, the middle disinfectant source 130 may be a UV source, and the outer sources 130 may be cold plasma sources. Alternatively, the middle source may be a cold plasma source and the two outer sources may be a UV source.

Figure 2:
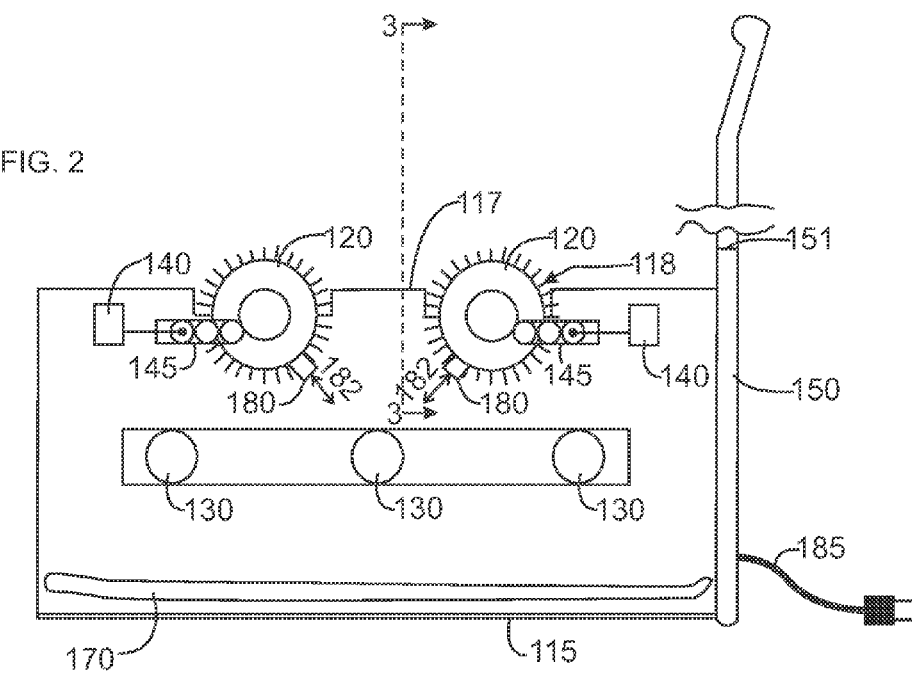
FIG. 2 is an exemplary side view of a cleaning and disinfecting apparatus, according to an embodiment of the invention.

FIG. 2 is an exemplary side view of a cleaning and disinfecting apparatus 100, according to an embodiment of the invention. FIG. 2 shows the support base 110 having a lower surface 115 and an upper surface 117. FIG. 2 further shows the cleaning rollers 120 and the disinfectant sources 130 substantially within the support base, with a top portion of the cleaning rollers 120 protruding through complementary openings 118 in the upper surface 117. The upper surface 117 also includes an upper surface window 119 (shown as dotted lines in FIG. 1). Depending on the application, i.e., whether the disinfectant source 130 is a radiation source or a charged particle source, the window 119 may be a transparent material or may be a material having openings to allow the charged particles through.

As shown the apparatus 100 also includes a debris collection tray 170 below the rollers 120 at the lower surface 115 for collecting debris removed from the footwear or foot. The collection tray 170 may be mounted for sliding into and out of the support base 110. Also shown are cleaner supply cartridges 180 which may be included, for supplying cleaner to the cleaning rollers. The cleaner supply may be a solid or a liquid cleaner, and the cleaner supply cartridges 180 may be movable into and out of contact with the rollers. This movement into and out of contact with the roller 120 may be facilitated by an actuator, outlined below. Arrows 182 show the displacement movement of the disinfectant cartridges 180 from an engaged position to a disengaged position. According to one embodiment, the cleaner supply cartridge 180 supplies liquid cleaner to the roller 120, so when the cartridge 180 is engaged with the roller 120, wet brush cleaning is activated. Dry brush cleaning may be performed when the cartridge 180 is retracted from the roller 120.

FIG. 2 shows bidirectional motors 140 which are provided for driving the cleaning rollers 120. FIG. 2 also shows gear trains 145 through which the cleaning rollers 120 are rotated. Because the motors 140 are bidirectional, the cleaning rollers may be optionally rotated in the same direction or may be rotated in opposite directions. It should be noted that even though FIG. 2 shows one motor 140 per cleaning roller 120, other embodiments may have a single motor 140 for driving all the rollers 120 by means of a gear train that allows the single motor 140 to drive all the rollers 120.

FIG. 2 also shows an arm 150 that extends vertically from the support base 110. A lower portion of the arm 150 is attached to the support base 110. Gripping handles 155 are formed at an upper portion of the arm 150. A user my grip the handles 155 for support and balance when cleaning and disinfecting her shoes. The arm 150 may include a telescoping joint 151 to adjust according to a user's height. The cleaning and disinfecting apparatus 100 may be powered by any known means. For example, the apparatus 100 may be powered via a power cord 185, which may be attached to a conventional wall unit. An ON/OFF switch may be positioned at an upper part of the arm 150 to power up and shut off the apparatus 100.

FIG. 3 is an exemplary sectional front view of a cleaning and disinfecting apparatus through line 3-3 of FIG. 2. FIG. 3 shows one of the cleaning rollers 120 being mounted on an axle 320 about which the roller 120 rotates. FIG. 3 further shows the gear train 145 connected to the roller for delivering rotational movement powered by the motor 140. Also shown in the disinfectant cartridge 180 extending the entire width of the cleaning roller 120, and the collection tray 170.

FIG. 3 also shows a control panel 160 which a user may use to manually control the operation of the apparatus 100. The control panel may include an input device 162 such as a keypad, touchpad, or the like, and a display 164, such as for example, an LCD or flat screen. FIG. 4 is a block diagram of a control arrangement that may be included in the cleaning and disinfecting apparatus 100, according to an embodiment of the invention. As shown, the apparatus 100 includes a central processing unit (CPU) 210, a main memory 220, the input device 162, the display device 164, the bidirectional motor 140, the disinfectant source 130, which as outlined above, may be a radiation source or a charged particle source. Also illustrated is the actuator 181 associated with each supply cartridge 180 for moving each cleaner supply cartridge 180 into and out of engagement with the respective cleaning roller 120. Each of the constituents of the controller arrangement is connected to one another through a bus 205, so that necessary information can be transmitted to the constituent elements.

The CPU controls the operation of the cleaning and disinfecting machine based on input commands from the user via the input device 162 and a simple operations program stored on the main memory 220. Thus in operation, when a user stands on the upper surface 117 of the support base 110, the user may control the speed, and direction of rotation of the respective cleaning rollers, via the control panel 160. Thus, rollers may be rotated in similar or opposite directions. A user may also control whether to engage the cleaning supply cartridge 180 with roller 120 when cleaning, allowing for wet or dry cleaning. Alternatively, a user may decide if to use the cleaning rollers 120 only or to use the disinfectant sources 130 only, or if to use both rollers and disinfectant sources simultaneously. Therefore for example, a user may, via the control panel, shut off the cleaning rollers 120 and activate the disinfectant sources 130 only.

What has been described and illustrated herein are preferred embodiments of the invention along with some variations. The terms, descriptions and figures used herein are set forth by way of illustration only and are not meant as limitations. For example, although the cleaning and disinfectant apparatus is outlined for working on footwear, the apparatus may also be used to clean and disinfect feet. Those skilled in the art will recognize that many variations are possible within the spirit and scope of the invention, which is intended to be defined by the following claims and their equivalents, in which all terms are meant in their broadest reasonable sense unless otherwise indicated.

What is claimed is:

1. A cleaner and disinfectant for footwear, comprising:
    a support base having an upper surface with an upper surface window, a lower surface, one or more side surfaces, and a hollow interior within the upper surface, the lower surface, and the one or more side surfaces;
    a plurality of spaced-apart rotatable cleaning rollers positioned within the hollow interior of the support base, wherein at least a portion of the each of the plurality of the spaced-apart rotatable cleaning rollers extends through the upper surface;
    a plurality of spaced-apart disinfectant sources projecting one of UV radiation, nano UV radiation, cold plasma, or non-thermal plasma through the upper surface window of the support base;
    one or more bidirectional motors;
    a gearing arrangement attached to the one or more bidirectional motors and the plurality of spaced-apart rotatable cleaning rollers for rotating each elongated brush in a desired direction;

a control panel having user controls to control the operation of the cleaner and disinfectant;

an arm attached to and extending upwards from the support base; and handles attached to an upper portion of the arm for user engagement when a user is standing on the cleaner and disinfectant, wherein the control panel is positioned on an upper portion of the arm.

2. The cleaner and disinfectant of claim 1, wherein there are two cleaning rollers and 3 disinfectant sources, arranged in an alternating relationship.

3. The cleaner and disinfectant of claim 2 wherein the controls allows a user to control the cleaning rollers so that they may optionally be rotated in the same direction or in directions opposite to each other, or may optionally be stopped to allow for disinfecting only via the disinfectant sources.

4. The cleaner and disinfectant of claim 3 further comprising:

a removable debris collection tray positioned within the hollow interior of the support base, beneath the plurality of spaced-apart rotatable cleaning rollers.

5. The cleaner and disinfectant of claim 3 further comprising:

one or more cleaning supply cartridges within the hollow interior of the support base, each of the one or more cleaning supply cartridges associated with one of the one or more cleaning rollers, each cleaning supply cartridge movable into an out of engagement with an associated cleaning roller for supplying cleaner to the associated cleaning roller.

* * * * *